United States Patent

Long, II

(10) Patent No.: US 6,783,951 B2
(45) Date of Patent: Aug. 31, 2004

(54) PROCESS FOR PRODUCTION OF CAROTENOIDS, XANTHOPHYLLS AND APO-CAROTENOIDS UTILIZING EUKARYOTIC MICROORGANISMS

(76) Inventor: Thomas Veach Long, II, 112 Cypress Ave., Wrightsville Beach, NC (US) 28480

( * ) Notice: Subject to any disclaimer, the term of this patent is extended or adjusted under 35 U.S.C. 154(b) by 339 days.

(21) Appl. No.: 09/793,382

(22) Filed: Feb. 26, 2001

(65) Prior Publication Data

US 2002/0015978 A1 Feb. 7, 2002

Related U.S. Application Data

(60) Provisional application No. 60/184,543, filed on Feb. 24, 2000.

(51) Int. Cl.⁷ .......................... C12P 23/00; A01N 65/00
(52) U.S. Cl. ......................... 435/67; 424/93.1
(58) Field of Search .............................. 424/93.5, 93.1; 426/3; 435/67

(56) References Cited

U.S. PATENT DOCUMENTS 5,340,594 A * 8/1994 Barclay

OTHER PUBLICATIONS

Carrera Rodriguez, R.A. et al., Isolation of Astaxanthin from Marine Thraustochytrids (Zoosporic Marine Fungi). Abstracts of the 98th General Meeting of the American Society for Microbiology. May 1998, p. 394, abstract 0–3.

* cited by examiner

Primary Examiner—Christopher R. Tate
Assistant Examiner—Randall Winston
(74) Attorney, Agent, or Firm—Pierce Atwood; Kevin M. Farrell; Janann Y. Ali

(57) ABSTRACT

Disclosed is a method for producing an effective amount of one or more carotenoid, xanthophyll, or apo-carotenoid pigments from a microorganism from the Order Thraustochytriales. Suitable microorganisms put forth are of the genus Thraustochytrium and Schizochytrium. Preferred culture conditions and mediums are discussed. Examples are given of production of specific pigments, such as β-carotene, lutein, adonirubin, canthaxanthin, and astaxanthin, as are examples of methods of isolation of the pigment from the microorganism. Also disclosed is a food product that contains a microorganism from the Order Thraustochytriales, the microorganism having produced internally an effective amount of one or more carotenoid, xanthophyll, or apo-carotenoid pigments. The food product is used in a method for delivering one or more of the pigments to an animal or human for either pharmaceutical, nutritional or coloration purposes, by feeding the food product to the animal or human.

19 Claims, No Drawings

PROCESS FOR PRODUCTION OF CAROTENOIDS, XANTHOPHYLLS AND APO-CAROTENOIDS UTILIZING EUKARYOTIC MICROORGANISMS

This application claims priority to provisional Application No. 60/184,543, titled "PROCESS FOR PRODUCTION OF CAROTENES, XANTHOPHYLLS AND APO-CAROTENOIDS UTILIZING EUKARYOTIC MICROORGANISMS", filed Feb. 24, 2000, the contents of which are incorporated herein by reference.

BACKGROUND OF THE INVENTION

Carotenoids are a class of biochemicals consisting of the carotenes. Xanthophylls are a related class of biochemicals and are the oxygenated derivatives of carotenoids. The prefix "apo" with an associated number or locant, signifies that all of the carotene molecule beyond that indicated part has been replaced by hydrogen atoms. Because these molecules contain a long series of conjugated double bonds, they often are highly colored, most often with red-to-yellow pigmentation. The most familiar carotenoid is β-carotene, which is commonly found in carrots, in sweet potatoes and other yellow vegetables, and in green, leafy vegetables such as spinach and kale. The carotenoids, xanthophylls and apo-carotenoids have value as both colorants and nutritional dietary supplements.

β-carotene is used as a food additive both as a colorant and a dietary supplement (Bauerfeind, J. C., et al. (1971) "Use of carotenoids." In: *Carotenoids*. O. Isler et al. (eds.), Halsted Press, New York, pp.743–770.). In these applications, the usual chemical form of βcarotene is the all-trans configuration, which is the isomer found in root vegetables and in the synthetic material produced by the principal manufacturing technologies.

β-carotene has been indicated to play a role in the prevention of cancer (Hennekens, et al., (1986) *Cancer* 58: 1837–1841; Krinsky, N. I. (1971) "Function." In: *Carotenoids*, O. Isler et al. (eds.), Halsted Press, New York, pp. 669–716.; Krinsky, N. I. (1988) *Clin. Nutr.* 7: 107–112; Mathews-Roth, M. M., and Krinsky, N. I. (1987) *Photochem. and Photobiol.* 40(4): 507–509; Krinsky et al., (1982) *J. Natl. Cancer Institute* 69: 205–210; Menkes, M., et al. (1986) *New England J. of Med.* 315: 1250–1254). Carotenoids such as β-carotene, and xanthophylls such astaxanthin, have also been shown to play central roles in the metabolism of the eye's macula and retina and in maintaining healthy vision (Handelman, G. J., and Dratz, E. A. (1986) "The role of antioxidants in the retina and retinal pigment epithelium and the nature of prooxidant-induced damage." *Adv. in Free Radical Biology and Medicine*, Vol. 2, pp. 1–89). Most Americans do not receive what is regarded by some as an optimal minimum dosage of approximately 75,000 I. U. (International Units) per day (Taylor, R. F., and Little. A. D. (1990) "Carotenoids: products, applications, and markets." *SPECTRUM Food Industry*, pp. 1–11).

The xanthophyll pigment astaxanthin is widely distributed in nature and is the predominant pigment in shrimp, crab, lobster, and salmonids. Additionally, it produces the red coloration of some birds such as flamingos and the scarlet ibis (Weedon, B. C. L. (1971) "Occurrence." In: *Carotenoids*, O. Isler et al. (eds.), Halsted Press, New York, pp. 29–60.). There is evidence that xanthophylls function as chemo-protectives. In addition, other xanthophylls, such as adonirubin and astaxanthin, may also act as nutraceuticals that prevent carcinogenesis through anti-oxidative, anti-free radical, or other mechanisms. The beneficial nutraceutical functions of the carotenes and xanthophylls extend to the prevention of heart attacks and strokes).

One of the most important uses of the xanthophylls is in animal feed. Astaxanthin provides the distinctive coloration for many multicellular organisms and generally must be obtained from a dietary source. When fish such as salmon, rainbow trout, red sea bream, or yellowtail are aquacultured, this pigment must be included as a dietary supplement in order to produce the coloration necessary for effective marketing (Committee on Animal Nutrition, National Research Council (1983) *Nutrient Requirements of Warmwater Fishes and Shellfishes*. National Academy of Science, pp. 55–57; Foss, P., et al., (1984) *Aquaculture* 41: 213–226; Foss, P., et al., (1987) *Aquaculture* 65: 293–305; Meyers, S. P., and Chen., H-M. (1982) "Astaxanthin and its role in fish culture," In: *Proceedings of the Warmwater Fish Culture Workshop*, Special Publication No. 3, World Mariculture Society, Charleston, S.C.; Torrissen, O. J. (1986) *Aquaculture* 53: 271–278; Torrissen., O. J., et al., (1987) "Pigmentation of salmonids-carotenoid deposition and metabolism." Northwest and Alaska Fisheries Center). Pigmentation has been achieved using arctic krill as a dietary supplement (Arai, S., et al., (1987) *Aquaculture* 66: 255–264), but this is expensive.

Canthaxanthin is also used as a food colorant, principally in pink grapefruit juice cocktail mixtures and in poultry, eggs, and aquacultured fish, where it is introduced through the feeds. There are no industrial microbial processes for the production of canthaxanthin, although it is found in the fungus that provides its name, *Cantharellus cinnabarinns*.

A recent study estimates that twenty percent of the carotene and xanthophyll supplement markets are dedicated to the natural form as opposed to synthetic materials (Taylor, R. F., and Little. A. D. (1990) "Carotenoids: products, applications, and markets." *SPECTRUM Food Industry*, pp. 1–11). The principal source of natural microbial βcarotene has been photoautotrophic microalgae *Dunaliella salinas* and *Dunaliella bardawil* (Ben-Amotz ET AL., (1990) *Tibtech* 76(5): 121–126; Ben-Amotz, A. (1986). "β-carotene enhancement and its role in protecting *Dunaliella bardawil* against injury by high irradiance." In: *Algal Biomass Technologies*, W. R. Barclay and R. P. McIntosh (eds.), J. Cramer, Berlin, pp. 132–147). Approximately one-third of the natural β-carotene produced by Dunaliella is the 9-cis isomer. The differentiation between the 9-cis and all-trans form of β-carotene has been claimed to be nutritionally important (Ben-Amotz et al., (1989) *J. Nutrition* 119: 1013–1019). A commercial obstacle to using Dunaliella as a source for β-carotene is the difficulty of extracting the pigments from the organisms. This difficulty in extraction correlates with a difficulty in bioexpression of the pigments (defined as the amount of pigment absorbed as a percentage of the amount consumed) when the Dunaliella organism is fed to an animal as a pigment source (Nonomura (1987) U.S. Pat. No. 4,680,314).

A recent comprehensive review (Johnson, E. A., and An, G-W. (1991) *Critical Reviews in Biotechnology* 11(4): 297–326) cites only two microbial species that are producers of astaxanthin. One is the green microalga Haematococcus, and the other is the yeast *Phaffia rhodozyma*. Production using Haematococcus has been attempted in photoautotrophic cultivation in open, fresh-water ponds. Unlike Dunaliella, Haematococcus cannot grow in highly-saline culture conditions, and the fresh-water ponds contaminate easily. Otherwise, production is in closed systems and is very costly.

Astaxanthin is also produced in the Phaffia yeast (An, et al., (1990) *Applied and Environmental Microbiology*, 55: 116–124; An, et al.(1991) *Bio/Technology* 9: 70–73). One difficulty that has limited the appeal of both Haematococcus and Phaffia as sources of astaxanthin is very low bioavailability and bioexpression of the astaxanthin in the intact organism, which is attributed to the strong cell walls.

The Thraustochytriales are a relatively obscure order of unicellular organisms rarely described in biology textbooks (Bahnweg, G., and Jackle, I. (1986) "A new approach to taxonomy of the Thraustochytriales and Lybrinthulales." In: *The Biology of Marine Fungi*, S. T. Moss (ed.), Cambridge University Press, London, pp. 131–140). Thraustochytriales are saprobs, feeding on plant detritus, and are common in marine and estuarine waters, growing naturally at a variety of salinities. Thraustochytriales are known to occur on marine macroalgae as well, and they are found in environments stretching from tropical waters to arctic and Antarctic environments. Reproduction is vegetative or involves the formation of zoospores, which escape through a variety of cleavage mechanisms to produce new sporangia.

Thraustochytriales are described as "eucarpic and monocentric, with an endobiotic rhizoidal system resembling chytrids but producing planonts like those of oomycetous fungi" (Ninet, L., and Renaut, O. (1975) "Carotenoids." In: *The Mycetozoans* Olive, L. S. (ed.), Academic Press, NewYork, pp. 529–545). The cell wall is composed of overlapping scales, and their sensitivity to environmental perturbation may well stem from this feature (Bartnicki-Garcia, 1988). Most of the research on these organisms has focused on taxonomic definition. (Emerson, R. (1950) *Ann. Rev. Micro.* 4: 169–200; Goldstein, S. (1965) *Am. J. Bot.* 50: 271–279; Margulis, 1970; Margulis et al., (1985) *BioSystems* 18: 141–147; Moss, S; (1986) "Biology and phylogeny of the Labrinthulales and Thraustochytriales." In: *The Biology of Marine Fungi*, S. T. Moss (ed.), Cambridge University Press, London, pp. 105–130; Perkins, F. O. (1974) *Veroff. Inst. Meeresforsch. Bremen, Suppl.* 5: 45–63; Perkins, F. O. (1976) "Fine structure of lower marine and estuarine fungi." In: *Recent Advances in Marine Mycology*, E. B. Gareth Jones (ed.), Elek Science, pp. 279–312; Ragan, M. A., and Chapman, D. J. (1978) *A Biochemical Phylogeny of the Protists*, Academic Press, New York, pp. 1–5, 147–168; Sparrow, F. K. (1960) *Aquatic Phycomycetes*. University of Michigan Press, Ann Arbor, pp. 37–38). This includes studies that employ chemical taxonomy based on fatty acid distributions (Ellenbogen et al., (1969) *Comp. Biochem. Physiol.* 29: 805–811; Findlay, R. H., et al. (1986) "Biochemical indicators of the role of fungi and Thraustochytrids in mangrove detrital systems." In: The *Biology of Marine Fungi*, S. T. Moss (ed.), Cambridge University Press, London, pp. 91–105). Aside from these fatty acid profiles, no biochemical characterization has been made. There is no literature report of the analysis of specific pigments, although there have been anecdotal reports of yellow-to-orange coloring of the ectoplasmic nets and speculation that some orange or red-colored species contain xanthophyll pigments (Barclay (1992), U.S. Pat. No. 5,130,242).

SUMMARY OF THE INVENTION

The present invention relates to a method for producing one or more carotenoid, xanthophyll, or apo-carotenoid pigments. The method comprises providing a microorganism from the Order Thraustochytriales capable of producing an effective amount of the desired pigment, culturing the microorganism under conditions of heterotrophic growth appropriate for effective production of the pigment, and then isolating the pigment from the cultured microorganism. Microorganisms put forth as suitable for this method are of the genera Thraustochytrium and Schizochytrium. Preferred culture conditions and medium are described. Examples are given of production of specific pigments, such β-carotene, lutein, adonirubin, canthaxanthin, and astaxanthin. The present invention also relates to a food product, comprising food material and a microorganism from the Order Thraustochytriales, the microorganism having produced internally an effective amount of one or more carotenoid, xanthophyll, or apo-carotenoid pigments. The food product is used in a method for delivering one or more pigments produced by the microorganism to an animal or human, by feeding the food product to the animal or human.

DETAILED DESCRIPTION OF THE INVENTION

The present invention is based on the finding that select microorganisms of the order Thraustochytriales, presently known to consist of the genera Thraustochytrium and Schizochytrium, are capable of producing large amounts of pigments such as carotenoids, xanthophylls and apo-carotenoids, when cultured under the appropriate conditions. The term "pigments" is used herein to generally refer to the carotenoid, xanthophyll, and apo-carotenoid molecules produced and isolated. It should be understood that although the term "pigment" carries a functional connotation (e.g., for use as a colorant), that many of the molecules produced, are useful for their nutritional/pharmaceutical properties as well as, or rather than, their characteristic color.

The ability of Thraustochytriales to generate carotenoid, xanthophyll, and apo-carotenoid pigments at commercially effective levels was unknown prior to the present invention. Barclay (U.S. Pat. No. 5,130,242 (1992)) reports the isolation of some select organisms which exhibit coloration, and proposes that this coloration is due to the presence of carotenoids and xanthophylls. However, this is merely put forth as speculation as no characterization of the pigment produced from the microorganism has been disclosed in the art. Strains that have the ability to generate specific pigments at commercially effective levels are generated from natural isolates by a process of selective culturing. Commercially effective levels, as the term is used herein, refers to the generation of levels of pigment which are equal to or in excess of 10 mg total pigment/liter culture. As detailed in the Exemplification section below, strains initially isolated and developed produced upwards of 15–30 mg total pigment/liter culture. Selective culturing of these strains has since led to their developing increased production levels as high as 350 to 380 mg total pigment/liter culture.

A factor that contributes to the determination of a commercially effective level of pigment production is the cost of production, which includes culturing the organism and purification of the pigment(s) produced. Unexpectedly, it has been found that the microbes may be cultured for pigment production relatively inexpensively utilizing common media components, and also that the pigments can be extracted from the microorganism by relatively inexpensive methods.

Further contributing to the determination of a commercially effective level of pigment production is the stability of the pigments within the microorganisms. It has been determined that the pigments stored in dried or frozen microbes do not undergo appreciable levels of oxidation, or breakdown by any other means of chemical decomposition.

One aspect of the present invention relates to a method for producing one or more carotenoid, xanthophyll, or apo-carotenoid pigments. The method is accomplished by first providing a microorganism from the Order Thraustochytriales capable of producing an effective amount of the carotenoid, xanthophyll or apo-carotenoid. The microorganism is then cultured under conditions of heterotrophic growth appropriate for effective production of the desired carotenoid, xanthophyll, or apo-carotenoid pigment. Following generation of the pigment in the culture, the pigment is isolated from the cultured microorganism.

Carotenoid, xanthophyll, and apo-carotenoid are broad categories of pigments, each of which include several specific molecules. Experiments detailed in the Exemplification section below indicate that the microbes are useful for producing a number of these specific pigment molecules. Examples of carotenoids which can be generated are βcarotene and lutein. Examples of xanthophylls which can be generated are adonirubin, canthaxanthin, and astaxanthin. Pigment production is non-exclusive, as more than one pigment type (carotenoid, xanthophyll or apo-carotenoid) is usually present in the total pigment produced. Further, more than one specific pigment molecule of a given pigment type is generally produced.

Not all Thraustochytriales produce the pigments, and production is generally only under specific circumstances of culture. Various strains of the Thraustochytriales order have been isolated from nature for their ability to produce the pigments. These strains have been studied for the growth conditions which enhance pigment production, and many have been further selected for increased production. It may be beneficial to further identify or develop additional strains which possess increased proficiency at generating a desired pigment or pigments, or to further augment growth conditions in order to optimize production. This type of development via selection is within the ability of one of average skill in the art through routine experimentation, given the guidance provided in the Exemplification section below. Such Thraustochytriales microorganisms which also produce additional useful materials, such as Omega-3 and or Omega-6 fatty acids, may also be identified or developed.

The microorganism is cultured under conditions of heterotrophic growth appropriate for effective production of the desired pigment(s). Heterotrophic growth is defined herein as growth on media which provides an assimilable carbon source in the presence of oxygen. Production of one or more specific pigments is enhanced through manipulation of the culture conditions (e.g., media supplied and time in culture). In one embodiment, the media contains one or more sugars as a primary carbon source (e.g., glucose, corn syrup, dextrose). In another embodiment, the primary carbon source is a lipid molecule which comprises carbon chains from eight to thirty carbons in length (e.g., twelve, fourteen, sixteen, eighteen, twenty, and twenty-two carbon lengths are particularly useful). A mixture of such lipid molecules can also be used. In a preferred embodiment, the primary carbon source is a seed oil. Alternatively, or additionally, oleic, linoleic, gamma-linoleic, linoleic acids in the form of free fatty acids, triglycerides or phospholipids, may also be used. In order for the microorganism to produce pigment in an effective amount, the medium must additionally contain thiamine hydrochloride, a phosphate source, and a microbial growth factor source in sufficient amounts to promote sustained growth of the cultured microorganism. Suitable sources of these components are described in the Exemplification section below.

Culturing is preferably under aerobic conditions, especially wherein a high dissolved oxygen concentration is maintained. In a preferred embodiment, growth is at 0.5–1.0 vvm aeration. Large quantities of product can be obtained when the organism is grown via fermentation, and especially where nutrient medium is continually added to the culture growth container and cells and media of equal volume are removed. βcarotene, canthaxanthin, adonirubin, and astaxanthin, as well as other carotenoids, xanthophylls and apo-carotenoids, are produced under fermentation conditions as classic secondary metabolites. The initial pigment produced is β-carotene, and, when the fermentation is run under continuous feed conditions (continuous fermentation), this chemical can be produced in greater than ninety percent yield, as a proportion of total pigment. Canthaxanthin, adonirubin, and astaxanthin apparently are produced sequentially by increasing oxygenation of the βcarotene parent. As the natural reaction process proceeds, astaxanthin levels of greater than seventy percent, as a percentage of total pigment, can be achieved.

Preferably, the culture medium has a pH of from 4.0 to 9.0, and the growth temperature is from 12.5° C. to 40 C. The stage of growth influences pigment production. Generally, pigment production is highest during steady state growth, so prolonging this state is optimal for production. It may be useful to manipulate the culture conditions at various stages in production (e.g., by the addition of a different carbon source) to enhance the production of one or more pigments. For instance, limiting or varying the nutrients in the medium during culturing can be performed to enhance the production of one or more specific pigments. In one embodiment, culturing is under nutrient limited conditions for an amount of time ranging from 3 to 240 hours.

Growth and pigment production can occur under culture conditions which have salinity equal to the strength of sea water (thirty-eight percent salinity) down to zero salinity. One or more salts normally found in sea water can be added to the growth medium to produce the salinity. Preferably, growth is in a saline water culture medium which comprises the full range of sea salts. The saline water culture medium may be made from sea water or alternatively using artificial sea salts to produce the desired composition. A composition of saline water culture medium which is equivalent to 60% sea water is optimal. However, lower and higher percent equivalents can also be used successfully.

In one embodiment, the microorganisms are cultured with photoassistance. Although Thraustochytriales microbes have been previously reported in the art to grow only in the absence of light, the Thraustochytriales microbes used in the present invention have been found to also grow well with photoassistance, especially using moderate to high intensity light.

Pigment is isolated from the microorganism upon adequate production. In a preferred embodiment, this is by extraction of total pigment from the microorganism using an organic solvent (e.g., acetone, hexane, ethyl acetate). Specific pigments can then be further isolated from the total pigment by their characteristic properties (e.g., color or solubility). Alternatively, specific pigments can be isolated directly from the microorganism.

It has been found that the ability to directly extract the pigments from the microorganism correlates with a high bioavailability. The term "bioavailability", as used herein, refers to how readily a component is taken up and utilized by an multicellular organism upon consumption of the producing microorganism. A component with high bioavailability is readily taken up by a consuming organism. A component with low bioavailability is taken up poorly or not at all. Feeding studies on salmon using the microorganisms containing the pigments produced conclusively indicate a high bioavailability of the pigments to a consuming organism. The high bioavailability of the pigments from the Thraustochytriales organisms is in sharp contrast to other microorganisms used in the art to produce the same pigments. High bioavailability is useful, in that ingestion of the whole microorganism by a multicellular organism, will deliver a useful amount of the pigment. Therefore, the intact microorganism or partially processed version thereof which retains the pigment, can be ingested as a method of delivery (e.g., by direct ingestion or formulation with a food product). In this respect, the microorganism itself, formulated for consumption, functions as a dietary supplement.

The Thraustochytriales microorganism which contains the pigment(s) described above is useful for its colorant properties as well as pharmaceutical and nutritional properties. As such, it may be formulated as an additive to a product in which coloration is desired. Formulations such as food additive, cosmetic additive and paint additive can be produced from the microorganism (either processed or unprocessed). Products which can be produced from incorporation of the additive are discussed below. An anti-oxidant (e.g., vitamin E, vitamin C, BHT, BHA, TBHQ, ethoxyquin, or a combination thereof) may also be incorporated into the microbial cell mass after harvesting or to the pigments after they have been extracted.

Another aspect of the present invention relates to a product which has as one ingredient the above described microorganism which has produced and contains internally an effective amount of one or more carotenoid, xanthophyll, or apo-carotenoid pigments. In one embodiment, the product is a food product. A food product is produced by the addition of the microorganism to a food material, however in some instances, the microorganism itself will be consider food material and thus will not necessitate further incorporation. The food product may contain the whole microorganism in any processed form convenient for production (e.g., freeze dried, dried, frozen). The microorganism may also be processed prior to incorporation in the product to increase bioavailability (e.g., via lysis). Alternatively, the food product may contain a portion of the microorganism (e.g., fractionated by size, solubility) separated from the whole, the remaining part necessarily also containing the pigment (s).

Food material into which the microorganism is incorporated is preferably palatable to the organism which is the intended recipient. This food material may have any physical properties currently known for a food material (e.g., solid, liquid, soft). The food material, as well as any other components of the food product, should not be of a chemical nature which destroys or destabilizes the pigments contained therein. It may also be useful to package the food product under non-oxidizing conditions, or to incorporate an anti-oxidant or other preservative into the food product. The food product is useful for enriching the diet of the recipient with the carotenoid, xanthophyll or apo-carotenoid pigments contained within. Useful food materials include, without limitation, animal feed used for livestock (e.g., cows, pigs, fowl), infant nutrition and other food material for human consumption.

In addition, the microorganism containing an effective amount of pigment(s) may alternatively be incorporated into a pharmaceutically acceptable carrier suitable for oral administration to an individual (e.g., human or other animal). Such a formulation would not necessarily be consumed for feeding purposes. Alternatively, a pharmaceutically acceptable carrier suitable for topical application may be utilized. Topical application may be for coloration of the skin (e.g., cosmetic) or for delivery of nutrients to the skin.

The microorganism containing an effective amount of pigment(s) may also be incorporated in other products as a colorant. For instance, the microorganism may be incorporated into a paint, a cosmetic, a skin-care item. It may also be incorporated into a product which is an environmental indicator, or an instrument such as a biosensor for use as a detection agent. Depending upon the composition of the product in which the microorganism is to be incorporated, it may be of benefit to microencapsulate the microorganism prior to incorporation, for instance to aid in even pigment distribution throughout the product or to aid in preservation of the pigment.

Another aspect of the present invention relates to a method for delivering one or more carotenoid, xanthophyll, or apo-carotenoid pigments, described above, to an animal or human. This is accomplished by feeding the food product described above, which contains the desired pigment (via containing the microorganism) to the animal or human. This method is useful for delivery of pigments with nutritional or pharmaceutical properties to a human or an animal. In addition, this method can be used to deliver pigments with desired coloration properties to an animal, for example to result in the animal, or a product of the animal (e.g., an egg from a chicken), exhibiting a desired color. Animals, as defined herein, include terrestrial as well as aquatic (fresh water, sea water, and brackish water) animals. In one embodiment, the animal is routinely raised or harvested for human consumption. This includes, without limitation bovine and porcine mammals, avians such as those used for poultry (e.g., chickens, ducks, turkeys, geese), and marine creatures such as those routinely harvested as sea food (e.g., fish, shrimp, shellfish and crustaceans). In another embodiment, the animal serves as food for an animal which is routinely raised or harvested for human consumption. For example, aquatic macroorganisms often consume smaller organisms, (e.g., krill, rotifers, and penaid shrimp). The smaller organisms, raised on a diet that includes the food product described above, used themselves as feed, would provide adequate dietary supplement to the larger macroorganism.

Exemplification

Microorganisms of the order Thraustochytrialis, are used to produce carotenoids, xanthophylls, and apo-carotenoids. The pigments produced are utilized in a variety of applications such as incorporation as colorants or pigments, or as nutrients (e.g., in animal feeds). These pigments may be used in the form of the raw microbial cell mass; as a cell mass that has been treated so as to lyse or disrupt the cells; as the extracted, crude pigment mixture; as a purified extract; or as the individual separated pigments from the extract.

The following is provided as an example of methods of culturing the microorganisms and isolating pigments produced, and should not in any way be viewed as limiting.

The microbes from the Thraustochytriales, comprised of the Thraustochytrids and the Schizochytrids and any combinations thereof or combinations with other microbially-produced materials, are used to produce carotenoids, xanthophylls, or apo-carotenoids. This process consists of culturing the microorganisms in a medium containing an assimilable carbon source, an organic nitrogen source, a microbial growth factor source, and a phosphate source in a water solution in which the salinity may vary from zero percent to that of full-strength sea water (thirty-eight parts-per-thousand). The source of the assimilable carbon may be a sugar or an oil containing lipid molecule with chain links from eight to thirty carbons. The necessary microbial growth factor is furnished by monosodium glutamate, yeast extract, tryptone, or corn steep liquor.

The Organism

Strains used in the following examples are all mutant derivatives of a wild type Thraustochytrium sp. These microorganisms are of a common occurrence in the world's oceans. They are abundant in waters and sediments of coastal areas and in estuaries. Populations of variable densities occur in the open oceans, where they are major constituents of the marine mycoflora.

Thraustochytria reproduce asexually forming sporangia containing zoospores, which are released through a partial disintegration of the sporangial wall. Occasionally, motile zoospores are seen. The cell wall has been reported to be composed of overlapping plates, which may be related to the ease of extraction of the cell pigments. Not all Thraustochytria produce carotenoid pigments. Producing species do so only in the presence of specific media components and in specific growth phases.

EXAMPLE 1

Culture Maintenance And Shake Flask Culture

Isolated colonies were transferred to 16×25 mm tubes containing 5 ml of the following medium:

| | |
|---|---|
| Dextrose | 30.0 g/l |
| Sea Salts | 21.0 g/l |
| Processed CSL | 75.0 ml/l |
| Thiamine HCl | 0.6 mg/l |

(CSL = Corn Steep Liquor)

This medium was made with distilled water, and the pH was adjusted to 7.3 before sterilization. After incubation for 7-to-10 days, the tubes were stored at 8-to-10 degrees centigrade. Transfers to newly-prepared culture tubes was made every 4-to-6 weeks. Slants were be made by adding a 1.2% agar solution to the above medium. Growth on agar slants tends to be slower compared to growth in liquid medium.

For growth in Erlenmeyer flasks, 250 ml capacity flasks containing 40.0 ml of the same medium used for culture maintenance tubes, were sterilized by autoclaving for twenty minutes at 20 psig. Flasks were inoculated using 0.2 ml from a 7-to-10 day old culture tube. The flasks were placed on an orbital shake table rotating at 200 rpm with the temperature controlled at 30° C.

On occasions, temperature excursions to 32° C. for several hours were observed to have no adverse effects on growth or pigment production. The growth phase was complete in 85 hours or less with some pigment formation, mostly β-carotene. During the following 3–4 days, subsequent oxidation lead to a reduction in the level of β-carotene and increased levels of xanthophylls, including astaxanthin.

A modification of the above described medium permitted a reduction in the amount of processed CSL required for growth in shake flasks by substituting, in part, monosodium glutamate (MSG).

| Medium Composition: | | | |
|---|---|---|---|
| Dextrose | 30.0 g/l | Processed CSL | 30.0 ml/l |
| MSG | 7.0 g/l | Sea Salts | 21.0 g/l |
| Thiamine HCl | 1.2 mg/l | | |

The medium was made with distilled water and the pH was adjusted to 7.3 before sterilization. The provided organisms were also capable of utilizing seed oils such as soybean oil, sunflower oil, rapeseed oil, linseed oil, and other like materials. They did not grow to any significant extent when a long-chain normal paraffin (e.g., hexadecane) was the primary carbon source.

Although growth and production of the carotenoids was obtained using these oils, the yields were substantially less than when dextrose was the principal carbon source. Investigation of the use of seed oil has been limited to experiments in shake flasks only, where the presence of oil may adversely affect oxygen transfer. It is entirely possible that improved yield would result from the progressive addition of oil during the course of fermentation in a fermenter. For screening purposes, 40.0 ml per 250 ml Erlenmeyer flask of the following medium was used:

| | |
|---|---|
| Seed Oil | 0.6 ml/flask |
| Processed CSL | 75.0 ml/liter |
| Sea Salts | 21.0 gms/liter |
| Thiamine HCL | 0.6 mg/liter |

The pH was adjusted to 7.3 with 50% KOH prior to the addition of the oil. Sterilization time was 20 minutes at 20 psig.

It was necessary to process the corn steep liquor since the non-essential solids in corn steep liquor tend to retard pigment formation. An example of the processing is:

1. One volume of CSL is diluted with one volume of distilled water containing 21.0 g/l of Sea Salts.
2. The pH is raised to 7.2 with 50% Sodium Hydroxide. This creates a very heavy precipitate, which is removed by centrifugation.
3. The somewhat turbid centrate is further treated by adding 5.0 g/l of powdered egg white (Farbest Brands, Louisville Ky.) and raising the temperature to almost the boiling point. As the albumin coagulates, it ties up the remaining solids, which results in a clear, sparkling "second centrate."

The CSL-to-water ratio should be adjusted, if necessary, to yield a solution such that 100 ml weighs approximately 110 gms. A volumetric yield of the first centrate should be 70–75% with a 100 ml weight of about 110 gms. The volumetric yield of the second concentrate will be 88–90%, and 110 ml will weigh about 110 gms. The overall volumetric yield will range from 65 to 70%.

EXAMPLE 2

Fermenter Operation

The fermenter referenced in this section was a New Brunswick BioFlo III. It is operated without baffles. Typically a medium of the following composition was used:

| Part I: | Dextrose | 120.0 g |
|---|---|---| dissolved in distilled water to yield a total volume of 500 ml. pH was not adjusted

| Part II: | Sea Salts | 21.0 gms |
|---|---|---|
| | Processed CSL | 75.0 ml |
| | Thiamine HCl | 2.5 mg |

The pH was adjusted to 7.3 with 50% KOH, and the total volume is adjusted to 500 ml through the addition of distilled water.

Part I was combined with Part II after sterilization to give a combined volume of 1.0 liter.

| FEED | |
|---|---|
| Processed CSL | 168.0 ml |
| Sea Salts | 4.8 gm |
| Thiamine HCl | 1.2 mg |

Volume was adjusted to 300 ml using distilled water. The pH was adjusted to 7.3 with 50% KOH. Feed Rate: continuous starting at log hour 24 at 42 ml per day. All sterilizations were for 20 minutes at 20 psig. Fermenter temperature was maintained at 30° C. RPM was set at 550, and air was set at 0.6 vvm. Inoculum: 5% from shake flask at log hour 72. After inoculation, the pH is 6.4–6.6 and gradually increased to 8.2–8.4 over the course of the fermentation. Based on observations of growth and pigment formation, controlling the pH in the 7.0–7.2 range should improve yields. When run in a continuous mode, a steady state was achieved when one fermenter volume was displaced by an equal volume of complete medium introduced over a 48-hour period. Antifoam (silicone based) was added to control a light surface foam during the growth phase.

EXAMPLE 3

Use Of Artificial Salts In The Media And Optimal Concentration Of Saline Solution Thraustochytrium sp. were inoculated in 250 ml flasks containing media that were prepared using 150 ml of saline solution, 24 g of glucose, 1.6 ml of a standard $KH_2PO_4$ solution, 1.6 ml of a standard thiamine solution, 2 drops of a Vitamin $B_{12}$ solution, and 24 g of modified yeast extract. The saline solution was varied in its concentration of artificial sea salt from a concentration equivalent to full-strength sea water to that of forty percent sea water. These were compared with a sea water saline solution at a concentration of sixty percent of full-strength sea water (thirty-eight percent salinity). The data obtained are provided in Table 2, below. These results indicate that the artificial saline solution was completely equivalent to the natural sea water solution in production of biomass and in production of pigment. They also demonstrate that a sixty percent concentration of full-strength sea water was optimal for these organisms. The composition of the artificial sea water material is provided in Table 1. The artificial sea water salt mixture was obtained from Rila Corporation (P.O. Box 114, Teaneck, N.J. 07666), and is given in Table 3.

| Medium: | | | |
|---|---|---|---|
| Glucose | 24 g | $KH_2PO_4$ | 1.6 ml |
| Thiamine HCl | 1.6 ml | Vitamin $B_{12}$ | 2 drops |
| Mod. Yeast Ext. | 24 g | | |

TABLE 1

Additions (by sample #, DW = Distilled Water):

| Exp# (Triplicate Flasks) | |
|---|---|
| 1 (1–3) | 100% Rila Salts: 150 ml Rila Sol. (38%) |
| 2 (4–6) | 80% Rila Salts, 20% DW: 120 ml Rila Sol. (38%), 30 ml DW |
| 3 (7–9) | 60% Rila Salts, 40% DW: 90 ml Rila Sol. (38%), 60 ml DW |
| 4 (10–12) | 50% Rila Salts, 50% DW: 75 ml Rila Sol. (38%), 75 ml DW |
| 5 (13–15) | 40% Rila Salts, 60% DW: 60 ml Rila Sol. (38%), 90 ml DW |
| 6 (16–18) | 60 ml DW, 90 ml Sea Water |

Results

TABLE 2

| Expt. # | ml Rila Salts* g/10 ml | Dry Weight mg/l | Total Pigment |
|---|---|---|---|
| 1 | 150 ml | 0.02456 | 0.75 |
| 2 | 120 ml, 30 ml | 0.02743 | 1.396 |
| 3 | 90 ml, 60 ml | 0.02996 | 2.6254 |
| 4 | 75 ml, 75 ml | 0.0326 | 2.2606 |
| 5 | 60 ml, 90 ml | 0.04253 | 2.0416 |
| 6 | 60% Sea Water | 0.03306 | 2.9686 |

TABLE 3

Rila Marine Mix (Artificial Sea Salt) Composition
The stock Rila Solution contains 38% salts (38 g/100 ml).

| Compound | Concentration (mg/100 ml water) |
|---|---|
| $Cl^-$ | 1913 |
| $Na^+$ | 1046 |
| $SO_4^{2-}$ | 260 |
| $Mg^{2+}$ | 126. |
| $Ca^{2+}$ | 49. |
| $K^+$ | 34.8 |
| Tris amino buffer | 3.2 |
| $Br^-$ | 2.7 |
| $BO_3^{3-}$ | 1.2 |
| $I^-$ | 0.897 |
| $Sr^{2+}$ | 0.350 |
| $Mn^{2+}$ | 0.050 |
| $F^-$ | 0.040 |
| $Zn^{2+}$ | 0.020 |
| $Fe^{3+}$ | 0.010 |
| $Co^{2+}$ | 0.007 |
| $Al^{3+}$ | 0.003 |
| $MoO_4^{2-}$ | 0.002 |
| $Rb^+$ | 0.0006 |
| $Li^+$ | 0.0006 |
| $Cu^{2+}$ | 0.0001 |

EXAMPLE 4

Continuous Fermentation

The fermentation was started in a batch mode using the following medium, which consisted of two parts that were prepared separately and then combined:

| Medium - Part I | |
|---|---|
| Corn sugar | 96.0 gm |
| Thiamine HCl | 1.6 mg |
| Distilled water was added to bring the final volume to | 400.0 mi. |
| Medium - Part II | |
| Processed corn steep liquor | 240.0 ml |
| Thiamine HCl | 1.6 mg |
| Sea Salts | 21.0 gm |
| Distilled water was added to bring the final volume to | 400.0 mi. |

The pH was adjusted to 7.3 with 50% potassium hydroxide. Both medium parts were sterilized for 25 minutes at 18 psi and combined after sterilization. The combined medium was cooled to 29.5° C. and inoculated with a selected strain of Thraustochytrium grown for 72 hours in shake flasks. Inoculum volume was equal to 5% of the fermenter volume.

The fermentation was carried out in a Bio-Flo III fermenter (New Brunswick Scientific Co.) with the agitation rate set at 550 rpm and the aeration rate fixed at 1.0 vvm. Temperature was controlled at 30° C. When the percent residual sugar dropped to 3%, a continuous feed and equal volume withdrawal to a collector bottle was initiated. The feed/withdrawal rate was set at 400.0 ml per day.

Feed medium consisted of:

Medium-Part I: Corn sugar 60.0 gm plus 0.8 mg Thiamine HCl made up to 500 ml with distilled water.

| Medium - Part II | |
|---|---|
| Processed Corn Steep Liquor | 150.0 ml |
| Sea Salts | 21.0 gm |
| Thiamine HCl | 2.0 mg |
| Distilled water was added to a final volume of | 500 ml. |

After sterilization, Parts I and II were combined. A steady state was achieved as evidenced by a constant sugar concentration and constant dry weight of bio-mass in the fermenter as measured daily. Typical results obtained are shown in the Table 4:

TABLE 4

| Days After Achieving Steady State | Percent Residual Sugar | Dry Weight Biomass gm/l | Total Pigment Fermenter mg/l | Total Pigment Collector mg/l |
|---|---|---|---|---|
| 1 | 3.05 | 22.7 | 12.93 | 15.33 |
| 2 | 3.60 | 25.2 | 14.90 | 13.38 |
| 3 | 3.50 | 24.9 | 15.26 | 16.30 |
| 4 | 3.77 | 24.3 | 19.0 | 19.55 |
| 5 | 4.06 | 26.3 | 10.63 | 23.52 |
| 6 | 3.91 | 29.8 | 23.48 | 24.00 |
| 7 | 3.62 | 23.6 | 31.12 | 29.50 |

EXAMPLE 5

Effect Of Salinity

Table 5 below shows the effect of salinity on astaxanthin and total red pigment formation in shake flask using the following medium:

| | |
|---|---|
| Corn Sugar | 30 g/l |
| Processed corn steep liquor | 60.0 ml/l |
| Thiamine HCl | 0.5 mg/l |

Combinations of sea water and distilled water were added to give the concentrations of sea water:

TABLE 5

| % Sea Water | mg/l Red Pigment | mg/l Astaxanthin |
|---|---|---|
| 100 | 6.24 | 2.02 |
| 90 | 6.23 | 1.96 |
| 80 | 6.80 | 2.17 |
| 70 | 7.88 | 2.20 |
| 60 | 8.18 | 2.24 |
| 50 | 7.20 | 2.12 |
| 40 | 8.20 | 2.08 |
| 30 | 7.90 | 2.11 |
| 20 | 4.48 | 0.78 |

EXAMPLE 6

Growth On Soybean Oil

A strain of Thraustochytrium (#2341), previously selected for its ability to grow when soy bean oil was provided as the primary carbon source, was used to inoculate a shake flask containing the following medium:

| | |
|---|---|
| Processed Corn Steep Liquor | 75.0 ml/l |
| Soy Bean Oil | 15.0 ml/l |
| Sea Salts | 21.0 gm/ |
| Thiamine HCl | 10.6 mg/l |
| Distilled Water | to 1.00 l |

The pH was adjusted to 7.3 before sterilization.

After growing for three days, 0.5% of whole broth was transferred to a second flask containing the same soybean oil medium. This selection process was repeated seven times. One drop from the final flask served to inoculate a culture maintenance tube, which, after inoculation, was used to inoculate three flasks containing the soy bean oil medium. Table 6 below, shows the average pigment formation compared with that of the original strain following seven days on a shaker.

TABLE 6

| | β-Carotene mg/liter | Astaxanthin mg/liter | Total Pigment mg/liter |
|---|---|---|---|
| Original Strain #2341 | 1.22 | 0.94 | 4.01 |
| #2341 after selection | 1.88 | 4.45 | 12.99 |

Similar results were obtained when the following vegetable oils were substituted for the soybean oil: sunflower oil, corn oil, rape seed oil, and Puritan™ oil.

EXAMPLE 7

Fed Batch Fermentation

Batch fermentation was conducted in a five-liter BioFlo III fermenter (New Brunswick Scientific Co.) using media containing 12% corn sugar, in addition to those shown below.

| Medium - Part I | |
|---|---|
| Processed Corn Steep Liquor | 240.0 ml |
| Sea Salts | 67.2 gm |
| Thiamine HCl | 8.0 mg |

Distilled water was added to make up a combined volume of 2200 ml. The pH was adjusted to 7.3 with potassium hydroxide (KOH). Parts I and II of the medium were sterilized separately and combined before inoculation. Sterilization was for twenty-five minutes at 10 psig. After cooling the medium to 30.C., the fermenter was inoculated with 160.0 ml of a seventy-two-hour-old shake flask culture of Thraustochytrium.

| Medium - Part II | |
|---|---|
| Processed Corn Steep Liquor | 240.0 ml |
| Sea Salts | 67.2 gm |
| Thiamine HCl | 8.0 mg |

Distilled water was added to make up a combined volume of 2200 ml. The pH was adjusted to 7.3 with potassium hydroxide (KOH). Parts I and II of the medium were sterilized separately and combined before inoculation. Sterilization was for twenty-five minutes at 18 psig. After cooling the medium to 30.0 C., the fermenter was inoculated with 160.0 ml of a seventy-two-hour-old shake flask culture of Thraustochytrium.

A feed medium was prepared as follows:

| Processed Corn Steep Liquor | 540.0 ml |
|---|---|
| Sea Salts | 3.75 mg |
| Thiamine HCl | 15.2 gm |

Distilled Water was added to bring the final volume to 1.0 liter. Sterilization conditions were identical to those given above, and continuous addition of this supplemental medium was begun at log hour 21 at a rate of 70.0 ml/day. The pH was not adjusted. Other operative conditions were: Aeration Rate=1.0 vvm (8.0 SCFHG); Stirring Rate=550 rpm; Temperature=30 C. In addition to the supplemental feed, 85.0 ml of 3% sulfuric acid was continuously pumped into the fermenter at a rate of 17.0 ml per day beginning on day 3 and ending on day 8. Typical data obtained are presented in Table 7.

TABLE 7

| | Residual | | Mg/Liter (HPLC) | | | | |
|---|---|---|---|---|---|---|---|
| Day | pH | Sugar % | BC | CA | AD | AS | Total P |
| 1 | 6.34 | 9.22 | TR | TR | TR | TR | TR |
| 2 | 5.10 | 7.52 | 0.14 | 0.32 | 0.52 | 0.71 | 1.69 |
| 3 | 7.41 | 7.00 | 1.65 | 1.09 | 2.11 | 3.47 | 8.32 |
| 4 | 7.67 | 6.15 | 3.14 | 1.64 | 3.54 | 6.10 | 14.42 |
| 5 | 7.70 | 5.21 | 4.84 | 1.73 | 4.69 | 8.15 | 19.41 |
| 6 | 7.93 | 4.73 | 6.14 | 2.36 | 6.22 | 11.06 | 25.78 |
| 7 | 7.76 | 4.06 | 6.57 | 2.44 | 6.95 | 12.73 | 28.43 |

TABLE 7-continued

| | Residual | | Mg/Liter (HPLC) | | | | |
|---|---|---|---|---|---|---|---|
| Day | pH | Sugar % | BC | CA | AD | AS | Total P |
| 8 | 8.05 | 3.58 | 6.06 | 3.99 | 7.93 | 15.01 | 32.99 |
| 9 | 7.61 | 3.38 | 5.58 | 4.75 | 8.11 | 15.40 | 33.84 |

BC = β-carotene;
CA = Canthaxanthin;
AS = Adonirubin;
AS = Astaxanthin;
Total P = Total Pigment

EXAMPLE 8

Extraction Of Pigment From Thraustochytrialis
Total Broth Extraction

The preferred method consisted of extracting the whole fermentation broth in a liquid/liquid type extractor using ethyl acetate or other suitable non-water-miscible solvents. When dealing with small volumes, an aliquot of the whole broth was conveniently extracted by shaking the sample for five minutes with an equal or greater volume of ethyl acetate. A 5 ml sample of fermentation broth and cells was taken from fermenter or flask. 5 ml of ethyl acetate was added. This mixture was shaken by hand or on shaker. Centrifugation was then performed (Beckman GPK Centrifuge) at 3800 rpm for 5 minutes. This separated the aqueous and solvent layers. The latter layer contained the pigment to be analyzed.

Extraction Of Cells Only

An alternative method required the separation of the cells from the aliquot of whole broth and the addition of acetone to the cells using a volume equal to or greater than the volume of the whole broth from which the biomass was isolated. Mixing the biomass with the solvent for one minute ensured the complete extraction of all pigment. This method can readily be adapted for larger quantities of cells in Soxlet-type extraction units. A 10 ml sample of cells plus broth was used. This was centrifuged at 3800 rpm for 10 minutes and the supernatant then removed. 10 ml of acetone was added and the mixture was shaken for 3 minutes. This was then centrifuged at 3800 rpm for 5 minutes and the sample pipetted. Alternatively, the pigment was analyzed by measuring the visible absorbance at 474 nm in acetone. An extinction coefficient E(1%) =2100 was used for astaxanthin and the other red pigments and E(1%) =2500 was used for β-carotene.

EXAMPLE 9

A Method For Improving The Quality Of Corn Steep Liquor

Corn steep liquor (CSL), when supplemented with thiamine, can supply all the nitrogen and other metabolites necessary for Thraustochytrialis growth and pigment formation. These useful properties were improved substantially be treating the corn steep liquor according to the following method. A quantity of corn steep liquor was diluted with water such that 100 ml of the resulting solution weighs 110 gms. The pH of the solution was raised to 7.0–7.5 by the addition of sodium hydroxide (NaOH). Resulting solids were separated by centrifugation. Powdered egg white was added to the centrate at a proportion of 3-to-6 gm/l. The mixture was then heated to 85–98° C.

Removal of the formed solids resulted in a sparkling clear solution. When this "processed" corn steep liquor was used in conjunction with other medium components, pigment production by Thraustochvtrialis was enhanced as shown below in Table 8.

| Shake flask medium per liter | |
| --- | --- |
| Corn sugar | 30.0 gm |
| Processed or raw CSL | 83.0 gm |
| Sea Salts | 21.0 gm |
| Thiamine HCl | 0.6 |

TABLE 8

Pigment production after 7 days on shake table:

| | Dry Weight (DW) gm/l | Astaxanthin mg/gm DW | Astaxanthin mg/liter |
| --- | --- | --- | --- |
| Processed CSL | 5.54 | 1.489 | 8.250 |
| Raw CSL | 6.06 | 0.763 | 4.625 |

Similar results were obtained when vegetable oil was substituted for sugar in the above medium.

EXAMPLE 10
Pigment And Analysis
Total Broth Extraction (Recommended)

A 5 ml. sample of the fermentation broth and cells was obtained from fermenter or flask. 5 ml. of ethyl acetone were added. This mixture was shaken by hand or on shaker, and then centrifuged (Beckman GPK Centrifuge) at 3800 rpm for 5 minutes. This separated the aqueous and solvent layers. The latter layer contained the pigment to be analyzed.

Extraction of Cells Only

A 10 ml. sample of cells plus broth was centrifuged at 3800 rpm for 10 minutes and the supernatant removed. 10 ml of acetone was added and the mixture was shaken for 3 minutes. This was then centrifuged at 3800 rpm for 5 minutes and the sample pipetted.

High Performance Liquid Chromatography (HPLC)

The separation of pigment products from an acetone extract of the cells or an ethyl acetate whole broth extraction was accomplished using an isocratic system of 10% acetone in hexane as the mobile phase and an HS-3 silica column as the stationary phase. Detection was by visible absorbance at 470 nm. At a mobile phase flow rate of 1 ml/ minute, the total run time was 6 minutes. Neither the acetone or ethyl acetate extract could be injected directly in this low packing volume column. The 10 microliters of acetone or ethyl acetate containing the sample was sufficient to de-activate the silica with resulting low resolution and broad peaks. Therefore, these solvents were evaporated under nitrogen, and the residue was dissolved in the mobile phase. The astaxanthin peak area was linear with injection volumes of 5–20 microliters and concentrations from 1.0–20.0 micrograms per ml. Astaxanthin standards were prepared in 10% acetone: 90% hexane formed aggregates in the solution that adhered to glass surfaces. Astaxanthin standards were, therefore, made up with acetone.

Alternatively, total pigment was analyzed by measuring visible absorbance at 474 nm in acetone. An extinction coefficient $E(1\%)=2100$ was used for astaxanthin and the red pigments and $E(1\%)=2500$ was used for βcarotene.

Recovery

The whole broth was extracted with ethyl acetate at room temperature. Solvent was removed by reduced pressure evaporation. The residue is dissolved in hexane and applied to the top of the column, and the column was washed in turn with hexane followed by hexane/acetone mixtures of increasing polarity. The pigments were eluted sequentially in order of their increasing adsorption affinities.

Results from a typical fermenter run are presented in Table 9.

TABLE 9

TYPICAL FERMENTER RUN
HIGH PERFORMANCE LIQUID CHROMATOGRAPHY ANALYSES IN MG/L

| Elapsed Time (hrs) | pH | Residual Sugar 0/0 | Dry Wt. gm/liter | Beta-car. | Cantha. | Adoni. | Astax. | Total Red Pigment | Total Pigment |
| --- | --- | --- | --- | --- | --- | --- | --- | --- | --- |
| Start | 6.78 | | 0.00 | 0.00 | 0.00 | 0.00 | 0.00 | 0.00 | 0.00 |
| 21.00 | 6.42 | 9.20 | 6.60 | 0.05 | 0.09 | 0.03 | 0.07 | 0.19 | 0.24 |
| 45.00 | 7.42 | 7.60 | 9.20 | 1.00 | 0.93 | 0.30 | 0.19 | 1.42 | 2.42 |
| 69.00 | 7.89 | 7.00 | 8.40 | 2.35 | 1.31 | 2.14 | 3.44 | 6.09 | 9.24 |
| 93.00 | 7.84 | 6.70 | 10.30 | 3.21 | 1.88 | 2.79 | 6.44 | 11.11 | 14.32 |
| 117.00 | 7.99 | 5.80 | 10.70 | 3.99 | 2.71 | 3.50 | 8.33 | 14.54 | 18.53 |
| 141.00 | 8.01 | 5.18 | 12.80 | 4.24 | 3.82 | 4.28 | 9.31 | 17.41 | 21.65 |
| 165.00 | 7.91 | 4.10 | 13.00 | 4.88 | 5.09 | 5.14 | 10.17 | 20.40 | 25.38 |
| 189.00 | 7.89 | 3.29 | 13.90 | 6.80 | 7.84 | 6.11 | 10.18 | 24.13 | 30.93 |
| 213.00 | 7.91 | 2.00 | 16.50 | 9.41 | 10.67 | 6.90 | 9.14 | 26.71 | 36.12 |
| 237.00 | 8.15 | 1.70 | 15.00 | 10.87 | 12.42 | 7.85 | 10.32 | 30.59 | 41.46 |
| 261.00 | 8.32 | 0.02 | 13.50 | 13.44 | 17.67 | 10.75 | 11.42 | 39.84 | 53.28 |

Beta-car. = β-carotene;
Cantha. = Canthaxanthin;
Adoni. = Adonirubin;
Astax. = Astaxanthin
N.B. Unidentified pigment components are not included in "Total Red Pigment" or "Total Pigment."
These include a significant component that is believed to be the cis-isomer of β-carotene, which averages approximately one-third the concentration of the trans-isomer reported. A total pigment value including all the pigment components would be 15–25% larger than the "Total Pigment" reported above.

What is claimed is:
1. A method for producing one or more carotenoid pigments or xanthophyll pigments, comprising:
 a) providing a microorganism from the Order Thraustochytriales capable of producing carolenoid or xanthophyll pigment;
 b) culturing the microorganism of step a) in liquid culture medium under heterotrophic growth conditions, the growth conditions and duration of culture period being appropriate for production of the carotenoid or xanthophyll pigment at a level of at least 10 mg total pigment per liter culture medium during the post-exponential stationary growth phase;

c) harvesting cells from the stationary growth phase culture of step b); and d) isolating the carotenoid or xanthophyll pigment from the harvested cells of step c).

2. The method of claim 1 wherein the microorganism of step a) is of the genus Thraustochytrium.

3. The method of claim 1 wherein culturing step b) is under fermentation.

4. The method of claim 1 wherein culturing step b) is under aerobic conditions.

5. The method of claim 1 wherein culturing step b) is with medium comprising one or more sugars as a primary carbon source.

6. The method of claim 1 wherein culturing step b) is in a saline water culture medium.

7. The method of claim 6 wherein the composition of the saline water culture medium is equivalent to a sixty percent concentration of full-strength sea water.

8. The method of claim 1 wherein the microorganism is grown with medium comprising seed oil as a primary carbon source wherein the lipid molecules comprise carbon chains from eight to thirty carbons in length.

9. The method of claim 8 wherein the medium comprises seed oil as a primary carbon source.

10. The method of claim 1 wherein culturing step b) is with a medium comprising microbial growth factor, a phosphate source, and thiamine hydrochloride.

11. The method of claim 1 wherein isolating step c) is via extraction of total pigment from the microorganism in an organic solvent.

12. The method of claim 11 wherein isolating step c) further comprises isolation of the carotenoids or xanthophylls from the total pigment.

13. The method of claim 11 wherein the organic solvent is selected from the group consisting of acetone, hexane, and ethyl acetate.

14. The method of claim 1 wherein the carotenoid is a carotene.

15. The method of claim 14 wherein the carotene is β-carotene.

16. The method of claim 14 wherein the carotene is lutein.

17. The method of claim 1 wherein the xanthophyll is selected from the group consisting of adonirubin, canthaxanthin, and astaxanthin.

18. The method of claim 1 wherein isolation step c) comprises isolation of the carotenoid or xanthophyll from the cultured microorganism as a mixture of total pigment produced.

19. The method of claim 1 wherein the microorganisms of step a) further produce Omega-3 and Omega-6 fatty acids.

* * * * *